United States Patent
Kajiyama et al.

(10) Patent No.: US 11,534,144 B2
(45) Date of Patent: Dec. 27, 2022

(54) ULTRASONIC PROBE AND ULTRASONIC DIAGNOSTIC APPARATUS FOR IMAGE NOISE REDUCTION BY SWITCHING NOISE OF THE SWITCHING POWER SUPPLY TO TRANSMISSION

(71) Applicant: Hitachi, Ltd., Tokyo (JP)

(72) Inventors: Shinya Kajiyama, Tokyo (JP); Shinta Takano, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 203 days.

(21) Appl. No.: 16/575,527

(22) Filed: Sep. 19, 2019

(65) Prior Publication Data

US 2020/0138415 A1    May 7, 2020

(30) Foreign Application Priority Data

Nov. 1, 2018 (JP) .............................. JP2018-206746

(51) Int. Cl.
*A61B 8/00*    (2006.01)
*A61B 8/08*    (2006.01)

(52) U.S. Cl.
CPC .............. *A61B 8/56* (2013.01); *A61B 8/4477* (2013.01); *A61B 8/483* (2013.01)

(58) Field of Classification Search
CPC ......... A61B 8/56; A61B 8/4477; A61B 8/483; A61B 8/54; G10K 11/346; G01S 15/8915
See application file for complete search history.

(56) References Cited

U.S. PATENT DOCUMENTS

| | | | | |
|---|---|---|---|---|
| 2006/0020205 | A1* | 1/2006 | Kamiyama | A61B 8/467 600/437 |
| 2008/0146930 | A1* | 6/2008 | Takeuchi | G01S 15/8925 600/447 |
| 2010/0040123 | A1* | 2/2010 | Iwata | G06F 11/3656 375/220 |
| 2010/0121194 | A1* | 5/2010 | Kondo | A61B 8/00 600/459 |
| 2010/0191121 | A1* | 7/2010 | Satoh | A61B 8/56 600/459 |

(Continued)

FOREIGN PATENT DOCUMENTS

| | | |
|---|---|---|
| JP | 2006-149720 A | 6/2006 |
| JP | 2012-065694 A | 4/2012 |
| JP | 2013-191940 A | 9/2013 |

OTHER PUBLICATIONS

Japanese Office Action received in corresponding Japanese Application No. 2018-206746 dated May 17, 2022.

*Primary Examiner* — Serkan Akar
*Assistant Examiner* — Amal Aly Farag
(74) *Attorney, Agent, or Firm* — Mattingly & Malur, PC

(57) ABSTRACT

An ultrasonic probe includes: a plurality of transducers that perform electro-acoustic conversion on transmission pulses applied thereto to generate a transmission beam of ultrasonic waves; and transmission/reception circuits that are provided so as to correspond to each of the plurality of transducers. The transmission/reception circuits set transmission/reception switching timings at which the ultrasonic waves are switched from transmission to reception independently for each of the plurality of transducers.

10 Claims, 11 Drawing Sheets

(56) References Cited

U.S. PATENT DOCUMENTS

| | | | | |
|---|---|---|---|---|
| 2011/0245677 A1* | 10/2011 | Sato | ............ | G01S 7/52079 |
| | | | | 600/447 |
| 2012/0113759 A1* | 5/2012 | Oshiki | ............ | G01S 7/5208 |
| | | | | 367/178 |
| 2012/0190986 A1* | 7/2012 | Sato | ............ | G01S 7/5208 |
| | | | | 600/459 |
| 2012/0316437 A1* | 12/2012 | Song | ............ | B06B 1/0207 |
| | | | | 600/437 |
| 2015/0223778 A1* | 8/2015 | Honjo | ............ | A61B 8/54 |
| | | | | 600/447 |
| 2017/0065260 A1* | 3/2017 | Arai | ............ | A61B 8/54 |
| 2018/0028153 A1* | 2/2018 | Kuroiwa | ............ | A61B 8/488 |
| 2019/0117196 A1* | 4/2019 | Choi | ............ | G01S 7/5202 |

\* cited by examiner

FIG. 2A
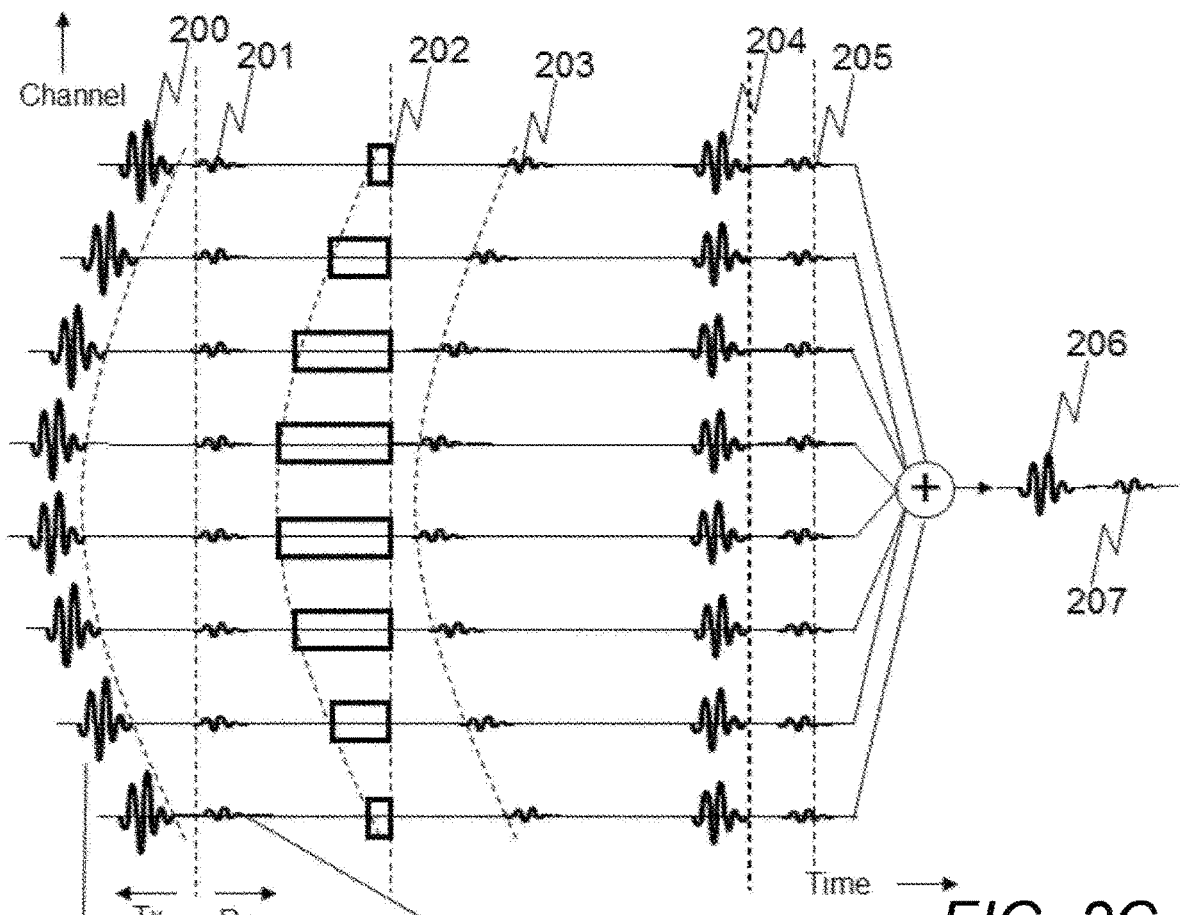
FIG. 2B
FIG. 2C
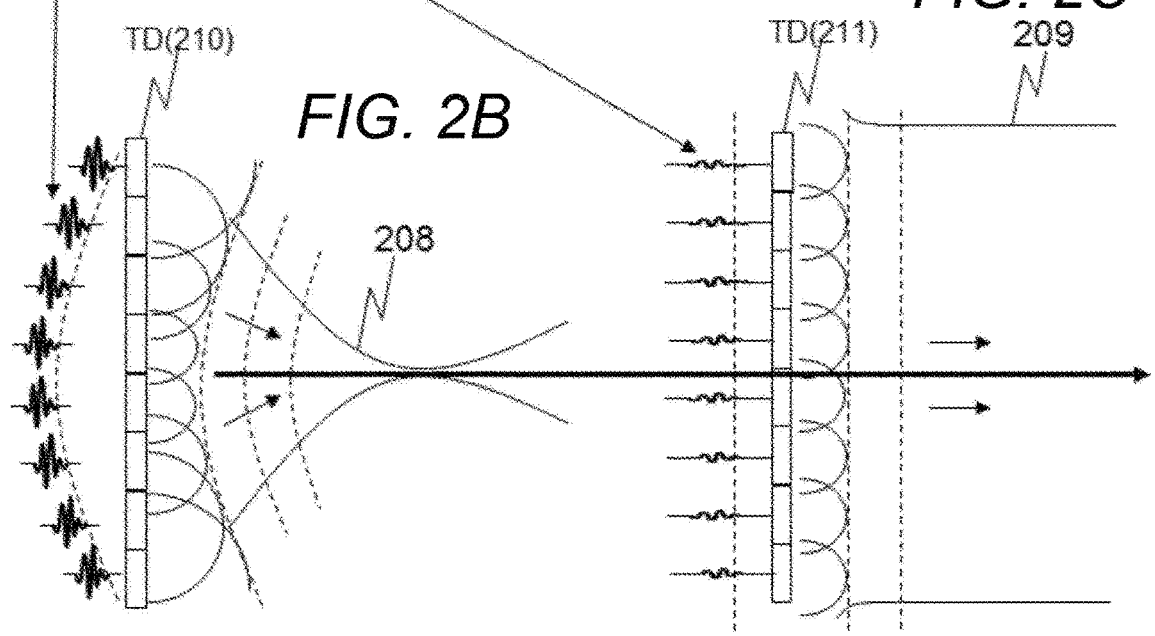

ULTRASONIC PROBE AND ULTRASONIC DIAGNOSTIC APPARATUS FOR IMAGE NOISE REDUCTION BY SWITCHING NOISE OF THE SWITCHING POWER SUPPLY TO TRANSMISSION

CROSS-REFERENCE TO RELATED APPLICATION

The present application claims priority from Japanese application JP 2018-206746, filed on Nov. 1, 2018, the contents of which is hereby incorporated by reference into this application.

BACKGROUND OF THE INVENTION

1. Field of the Invention

The present invention relates to an ultrasonic probe and an ultrasonic diagnostic apparatus.

2. Description of the Related Art

An ultrasonic diagnostic apparatus is a highly safe medical diagnostic apparatus that is non-invasive to a human body, and has an apparatus scale smaller than that of other medical image diagnostic apparatuses such as an X-ray diagnostic apparatus or a magnetic resonance imaging (MRI) apparatus. In addition, the ultrasonic diagnostic apparatus can display an aspect of movement of an inspection target such as, for example, pulsation of a heart or movement of a fetus in real time by a simple operation of simply putting an ultrasonic probe on a body surface. For this reason, the ultrasonic diagnostic apparatus plays an important role in today's medicine.

In the ultrasonic diagnostic apparatus, ultrasonic waves are transmitted into a subject by supplying high-voltage drive signals to each of a plurality of transducers embedded in the ultrasonic probe. Reflected waves of the ultrasonic waves generated by a difference in acoustic impedance of a biological tissue in the subject are received by each of the plurality of transducers, and an image is generated on the basis of the reflected waves received by the ultrasonic probe.

Specifically, in the transmission, acoustic pulses are focused by giving independent delays to the plurality of transducers and driving the transducers to perform beam forming and beam scanning of the ultrasonic waves. In the reception, in order to compensate for a difference between distances from a reflection point in a living body to the respective transducers, phasing processing such as giving the independent delays to the plurality of transducers to coherently align phases of signals with one another and adding the signals is performed.

As such, image capturing by the ultrasonic waves requires a transmission operation and a reception operation and inevitably involves switching from the transmission to the reception. In this case, a virtual image due to conversion of transmission/reception switching noises, which are electrical noises caused by the switching from the transmission to the reception, into sounds by the transducers and propagation and reflection of the sounds in the living body is problematic.

In recent years, an ultrasonic diagnostic apparatus capable of obtaining a three-dimensional stereoscopic image has been developed, and inspection efficiency can be improved by specifying an arbitrary cross section from the three-dimensional stereoscopic image to obtain a tomographic image. For three-dimensional image capturing, it is necessary to change the transducers in the ultrasonic probe from a conventional one-dimensional array to a two-dimensional array, that is, a 2D array, such that the number of transducers increases to a square of the number of transducers in a conventional ultrasonic probe.

Due to the 2D array, in addition to focusing in a long axis (X-axis) direction in a conventional 1D probe, focusing in a short axis (Y-axis) direction is performed, such that the sounds generated by the transmission/reception switching noises described above can be focused in both of the long axis and short axis directions. Therefore, in a 2D array probe, an influence of the virtual image due to the transmission/reception switching noises can be increased as compared with the 1D probe.

The transmission/reception switching noise is mainly caused by a transition from a turn-off state to a turn-on state of a transmission/reception separation switch installed between a high voltage transmission circuit and a low voltage reception circuit and protecting a reception circuit from a transmitted high voltage signal.

JP 2012-65694 describes a method of reducing a virtual image due to a switching noise of a switching power supply that supplies power to a transmission/reception circuit as an example of reducing a noise caused by switching.

JP 2012-65694 prevents the switching noises from being coherently added by controlling a relationship between a pulse repetition frequency (PRF) of transmission/reception of ultrasonic waves and a switching frequency of the switching power supply. Specifically, the switching frequency is determined so as to be asynchronous with the PRF in a B mode (image display by converting an amplitude of an echo into luminance) and an M mode (time-series display of echo intensity) to prevent the switching noises from being added at the same time phase when adding a plurality of echo signals obtained from the same scanning line.

SUMMARY OF THE INVENTION

As described above, JP 2012-65694 relates to a technology of reducing the virtual image due to the switching noise of the switching power supply that supplies the power to the transmission/reception circuit.

The switching of the switching power supply and the transmission/reception of the ultrasonic waves are independent events, and the switching frequency and the PRF can be determined independently of each other. However, the generation of the transmission/reception switching noises when switching the ultrasonic waves from the transmission to the reception is inevitable from the essence of ultrasonic image capturing in which the ultrasonic waves are transmitted and the echoes are then received, and cannot be treated as an event independent of a transmission/reception operation of the ultrasonic waves.

In addition, the transmission/reception switching noises that are electrically generated are directly superimposed on ultrasonic transducers and converted into sounds, and these sounds are transmitted into the living body even though they are unintended unnecessary generated sounds, such that the virtual image can be generated by echoes of the unnecessary transmitted sounds.

For this reason, a noise reduction approach different from the switching noise of the switching power supply is required for the virtual image due to the transmission/reception switching noises. JP 2012-65694 does not disclose reducing the virtual image due to the transmission/reception switching noises.

An object of the present invention is to reduce a virtual image due to transmission/reception switching noises in an ultrasonic diagnostic apparatus.

An ultrasonic probe according to an aspect of the present invention includes: a plurality of transducers that perform electro-acoustic conversion on transmission pulses applied thereto to generate a transmission beam of ultrasonic waves; and transmission/reception circuits that are provided so as to correspond to each of the plurality of transducers, wherein the transmission/reception circuits include transmission/reception switching timing setting circuits setting transmission/reception switching timings at which the ultrasonic waves are switched from transmission to reception independently for each of the plurality of transducers.

An ultrasonic diagnostic apparatus according to an aspect of the present invention includes: an ultrasonic probe that includes: a plurality of transducers that perform electro-acoustic conversion on transmission pulses applied thereto to form a transmission beam, transmission/reception circuits that are provided so as to correspond to each of the plurality of transducers and have transmission/reception switching timing setting circuits setting transmission/reception switching timings at which ultrasonic waves are switched from transmission to reception independently for each of the plurality of transducers, an addition circuit that adds outputs of a plurality of transmission/reception circuits, and a control circuit that controls the transmission/reception switching timings; and a main body device that receives an output of the addition circuit and transmits a predetermined control signal to the control circuit.

According to an aspect of the present invention, it is possible to reduce a virtual image due to transmission/reception switching noises in the ultrasonic diagnostic apparatus.

BRIEF DESCRIPTION OF THE DRAWINGS

FIG. 2A is a diagram illustrating an operation of performing transmission/reception switching simultaneously on all channels without performing randomization, FIG. 2B is a diagram illustrating electro-acoustic conversion of transmission pulses illustrated in FIG. 2A and a spatial behavior of a transmission beam, and FIG. 2C is a diagram illustrating electro-acoustic conversion of transmission/reception switching noises illustrated in FIG. 2A and a plane wave as a spatial behavior of the transmission/reception switching noises subjected to the acoustic conversion;

DESCRIPTION OF THE PREFERRED EMBODIMENTS

Hereinafter, embodiments will be described with reference to the drawings.

First Embodiment

Figure 1A:
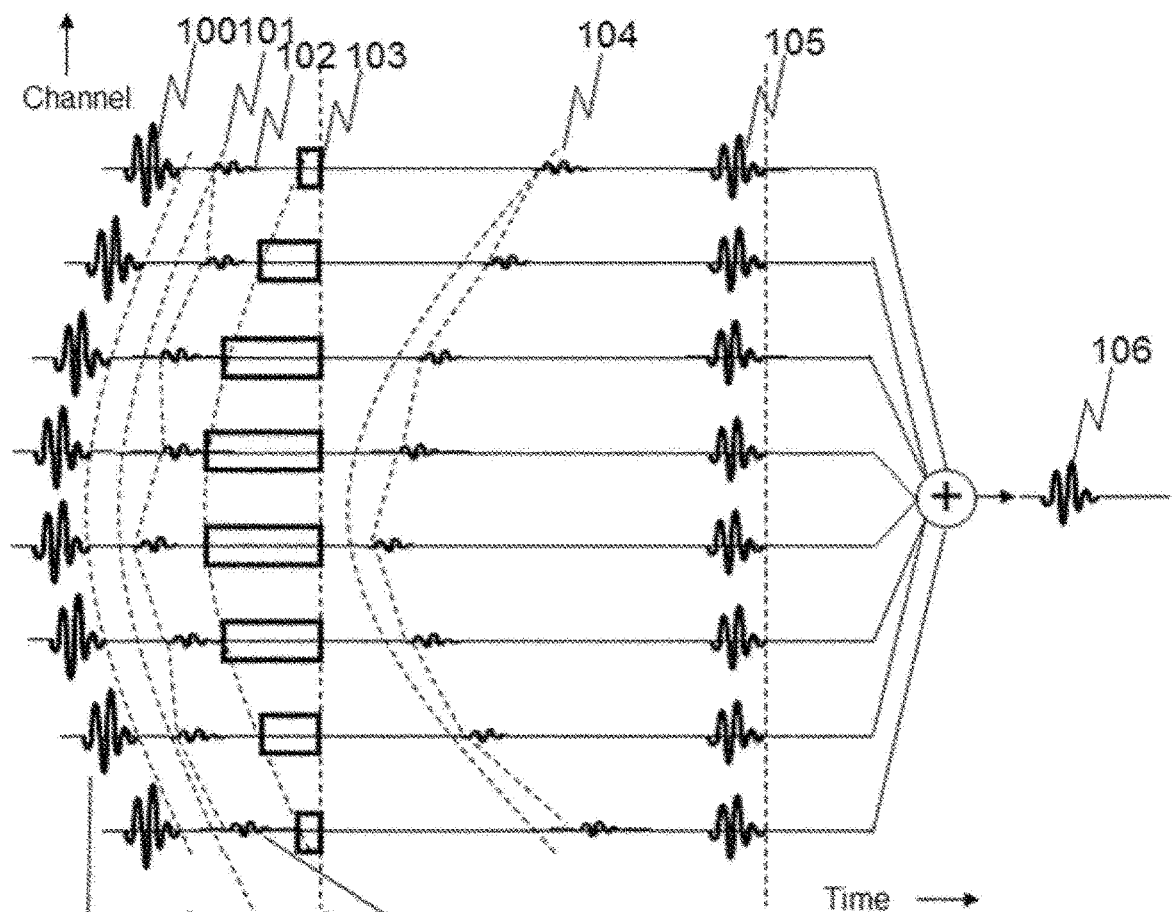
FIG. 1A is a diagram illustrating an operation of an ultrasonic probe according to a first embodiment.

An ultrasonic wave transmission/reception switching method in an ultrasonic probe according to a first embodiment will be described with reference to FIGS. 1A to 1C. Here, a horizontal axis of FIG. 1A is time, and a vertical axis of the FIG. 1A corresponds to a spatial arrangement of transducers (TD) 109. The respective waveforms indicate electrical signals of channels of the respective transducers (TD) 109. Here, Tx is transmission and Rx is reception.

Transmission pulses 100 are voltage pulse signals applied to the respective transducers (TD) 109. In order to perform beam forming with a desired directivity, delays are given to the respective transducers (TD) 109, and electro-acoustic conversion is performed by the transducers 109 (TD) to form a transmission beam like 107 (see FIG. 1B).

The respective transducer channels are switched to reception after transmission, and electrical transmission/reception switching noises 102 are generated by transitions of transmission/reception separation switches from a turn-off state to a turn-on state due to the switching between the transmission and the reception. Here, the transmission/reception switching noises 102 are obtained by randomly adding delays based on the same delay curve 101 as that of the transmission pulses 100. In this case, as illustrated in FIG. 1A, channels after the transmission ends are sequentially switched to the reception with the same delay curve 101 as that of the transmission pulses 100. Thus, a period in which the reception is not possible can be shortened and echoes returned from the vicinity of a body surface immediately after a transition to the reception can be received to image the vicinity of the body surface.

In addition, random delays are inserted between the channels with respect to the same delay curve 101 as that of the transmission pulses 100, and the respective channels are then switched to the reception. By giving the random delays between the channels, wave fronts of sounds generated by the transmission/reception switching noises 102 are disturbed, and the sounds are randomly propagated like a random wave front 108 (see FIG. 1C), such that a strong sound pressure is not generated.

Figure 1B:
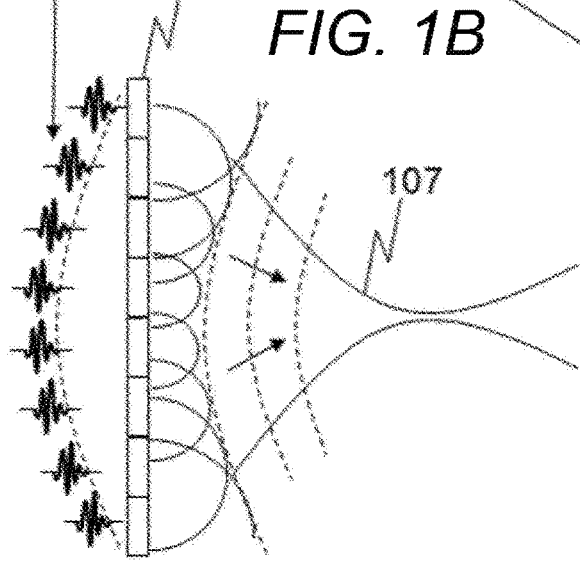
FIG. 1B is a diagram illustrating electro-acoustic conversion of transmission pulses illustrated in FIG. 1A and a spatial behavior of a transmission beam.

The respective channels are switched to the reception, and reception delays 103 are generated between the channels in order to perform reception with a directivity toward a direction of the transmission beam 107 (see FIG. 1B). The reception delays 103 are applied to the electrical transmission/reception switching noises 102, and switching noises are received by a delay curve 104. The delay curve 104 is transmission/reception switching noises after the reception delays 103. Since phases of the transmission/reception switching noises are not aligned with one another, the transmission/reception switching noises are not coherently added to become a strong noise.

On the other hand, in a case of echoes 105 (echo signals after the reception delays 103) reflected and returned in a living body, since differences in distances between a reflection point and the respective transducers (TD) 109 are compensated by the reception delays 103, phases of the echoes 105 are aligned with one another and the echoes are coherently added, such that a reception echo signal 106 after phasing addition is generated.

As such, according to the first embodiment, an ultrasonic beam is transmitted with a desired directivity like the transmission pulses 100, and coherent signals such as the echoes 105 are received by the reception delays 103, such that phasing addition can be performed on the reception echo signal 106 after phasing addition. On the other hand, unnecessary sounds generated by the transmission/reception switching noises 102 can be propagated randomly like the random wave front 108 to weaken the sound pressure. Thus, a virtual image caused by echoes of the unnecessary sounds by the transmission/reception switching noises 102 can be reduced.

As such, the ultrasonic probe according to the first embodiment includes a plurality of transducers (TD) 109 that perform electro-acoustic conversion on the transmission pulses 100 applied thereto to generate a transmission beam 107 of ultrasonic waves and transmission/reception circuits (1020 in FIG. 10) that are provided so as to correspond to each of the plurality of transducers (TD) 109. The transmission/reception circuits 1020 set transmission/reception switching timings at which the ultrasonic waves are switched from transmission to reception independently for each of the plurality of transducers (TD) 109. In addition, the transmission/reception circuits 1020 set timings at which a focusing direction of the ultrasonic waves by the transmission/reception switching noises generated when switching the ultrasonic waves from the transmission to the reception becomes a random direction, as the transmission/reception switching timings. In addition, the transmission/reception circuits 1020 set timings at which sounds generated by the transmission/reception switching noises 102 generated when switching the ultrasonic waves from the transmission to the reception are not focused on one point, as the transmission/reception switching timings.

Next, an effect of randomization of the transmission/reception switching timings in the first embodiment will be described with reference to FIGS. 2A to 2C.

First, an operation in a case of performing transmission/reception switching simultaneously on all channels without performing randomization will be described with reference to FIG. 2A.

Forming desired transmission pulses 200 is similar to FIG. 1A, and a focused transmission beam 208 is generated as illustrated in FIG. 2B. In a case where transmission/reception switching is performed simultaneously on all channels, sounds generated by transmission/reception switching noises 201 are propagated as plane waves 209 (see FIG. 2C). The electrical transmission/reception switching noises 201 are applied with reception delays 202, and are input to reception circuits by a delay curve 203 (transmission/reception switching electrical noises after the reception delays). As a result, the transmission/reception switching noises are not coherently added to become a strong noise. Echoes (echo signals after the reception delays) 204 reflected and returned in the living body become coherent by the reception delays 202 and are phased and added.

The plane waves 209 (see FIG. 2C) of the sounds generated by the transmission/reception switching noises 201 are not focused as a thin beam, but overlap a direction of the transmission beam 208 in a case of transmission in a directly downward direction. As a result, a reception focus is applied to echoes reflected and returned from a tissue interface in the living body, and transmission/reception switching electrical noise echoes 205 after the reception delays are coherently aligned with one another after the echoes (echo signals after the reception delay) 204. Therefore, a reception echo signal 206 after phasing addition is generated after the phasing addition, and after the reception echo signal 206 after phasing addition, a noise of a transmission/reception switching noise echo 207 after phasing addition remains to be a virtual image. As such, in a case where the randomization is not performed, the virtual image is generated by the transmission/reception switching noise echo 207 generated due to the transmission/reception switching electrical noise echoes 205.

Figure 3A:
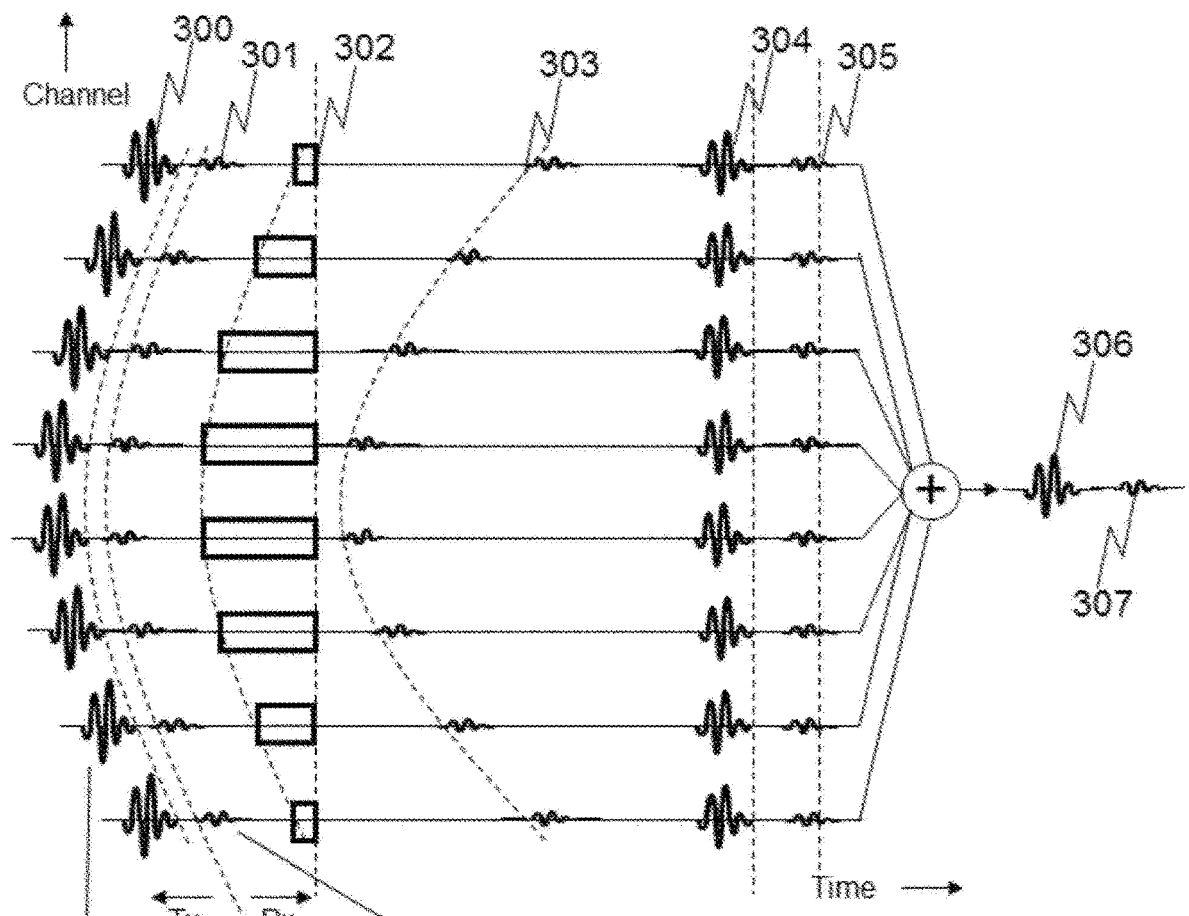
FIG. 3A is a diagram illustrating an operation of switching channels after transmission ends to reception without performing randomization.

Next, an operation of sequentially switching channels in which transmission ends to reception after the transmission as illustrated in FIG. 3A without performing randomization of transmission/reception timings will be described with reference to FIGS. 3A to 3C.

Figure 3B:
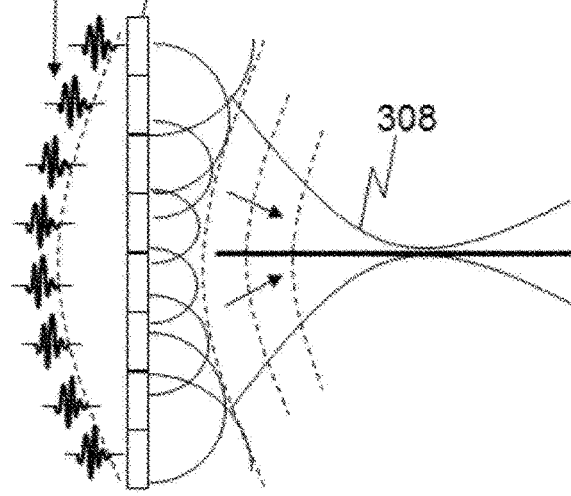
FIG. 3B is a diagram illustrating electro-acoustic conversion of transmission pulses illustrated in FIG. 3A and a spatial behavior of a transmission beam.
Figure 3C:
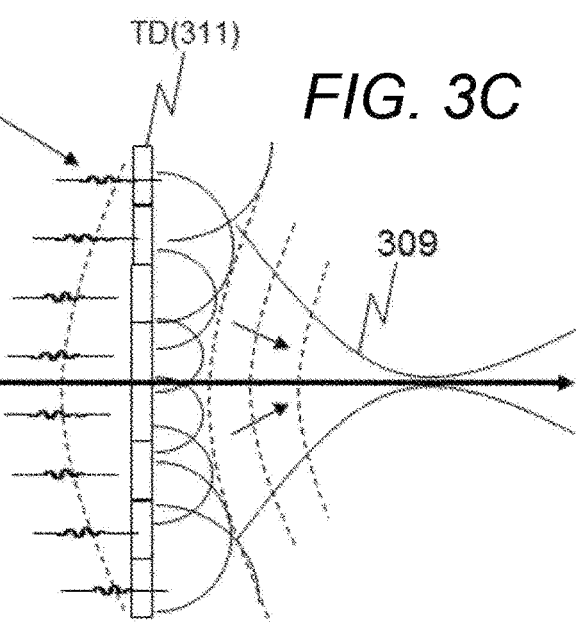
FIG. 3C is a diagram illustrating electro-acoustic conversion of transmission/reception switching noises illustrated in FIG. 3A and a beam as a spatial behavior of the transmission/reception switching noises subjected to the acoustic conversion.

As illustrated in FIG. 3A, transmission pulses 300 are transmitted with reception delays 302 to obtain a transmission beam 308 (see FIG. 3B). A delay curve of transmission/reception switching noises 301 becomes the same curve as that of the transmission pulses 300. For this reason, sounds generated by performing acoustic conversion on the transmission/reception switching noises 301 by transducers (TD) 310 form the same beam 309 (see FIG. 3C) as the transmission beam 308. Here, the beam 309 is a beam by the transmission/reception switching noises 301.

Transmission/reception switching electrical noises 303 after the reception delays generated by applying the reception delay 302 to the electrical transmission/reception switching noises 301 are not coherently aligned with one another. However, transmission/reception switching noise echoes 305 after the reception delays generated by reflection and return of the sounds by the transmission/reception switching noises 301 are coherently aligned with one another after echo signals 304 after the reception delays, such that a reception echo signal 306 after phasing addition is generated after the phasing addition and becomes a transmission/reception switching noise echo 307 after phasing addition to form a virtual image in the vicinity of a reception signal. As such, in a case where the randomization is not performed, the virtual image is generated by the transmission/reception switching noise echo 307 after phasing addition generated due to the transmission/reception switching noise echoes 305 after the reception delays.

In FIG. 3A, the transmission end channels are sequentially switched to the reception unlike FIG. 2A, and thus, there is an advantage that a period in which the reception is not possible can be shortened to image the vicinity of a body surface. However, the sounds by the transmission/reception switching noises 301 are focused in the same scanning direction as that of the transmission beam 308 like the beam 309 (see FIG. 3C) by the transmission/reception switching noises 301, such that a sound pressure becomes strong. For this reason, an influence of the virtual image becomes larger than that in FIG. 2A.

As described above, in the first embodiment, it is possible to make the period in which the reception is impossible shorter than that in FIG. 2A to image the vicinity of the body surface. Furthermore, by randomizing the transmission/reception switching timings between the channels, it is possible to avoid focusing of the sounds of the transmission/reception switching noises 301 as illustrated in FIG. 3A to reduce the sound pressure, resulting in a reduction of the virtual image.

Next, a circuit configuration for carrying out the first embodiment will be described with reference to FIG. 4.

Figure 4:
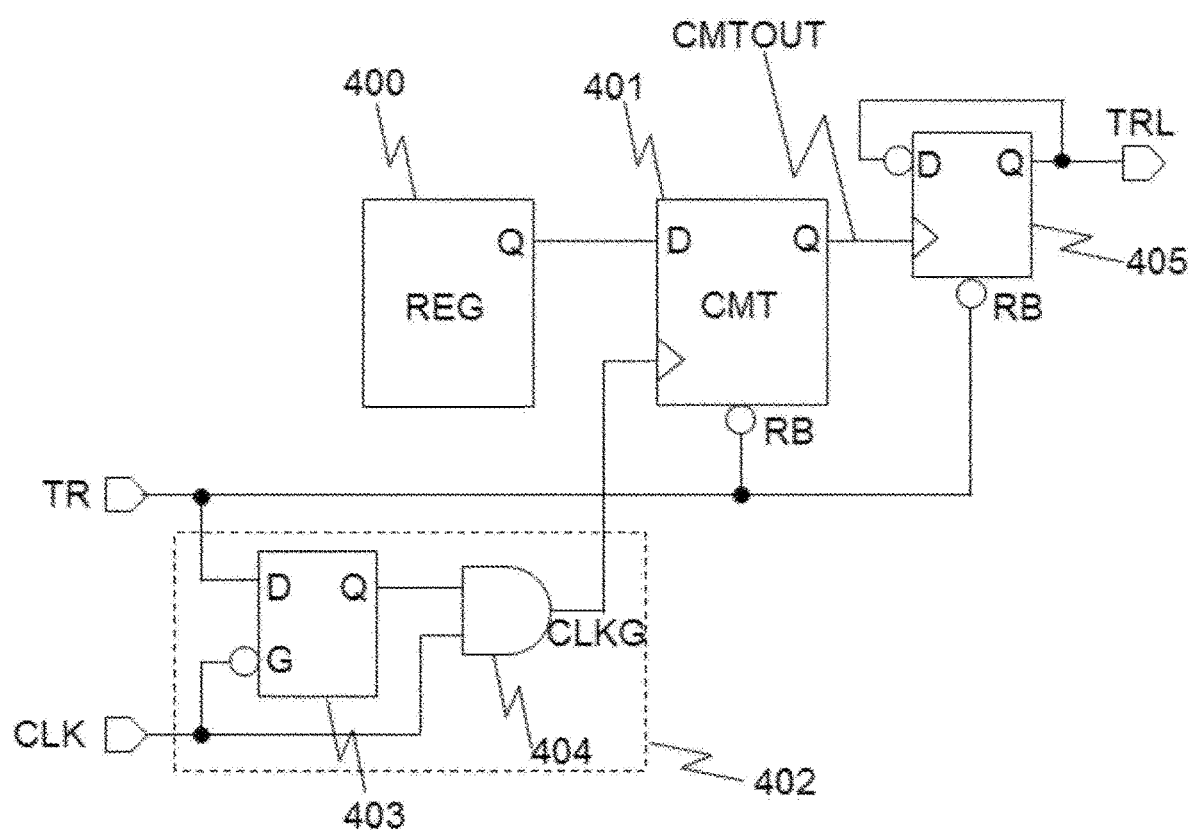
FIG. 4 is a diagram illustrating a configuration of a timing circuit including a register and a timer circuit which are arranged in each channel and realize independent and arbitrary transmission/reception switching timings in each channel.

As illustrated in FIG. 4, a register (REG) 400 and a compare match timer (CMT) 401 are arranged in the transmission/reception circuit (1020 in FIG. 10) of each transducer channel. The register (REG) 400 stores a value related to the transmission/reception switching timing, and stores different values for each channel. TR is a transmission/reception switching signal common to all channels, and is used as a trigger to generate a channel-local transmission/reception switching signal TRL delayed by a clock cycle of the value stored in the register (REG) 400. A flip flop (FF) 405 is a circuit for holding TR=1 even though CMTOUT returns to 0 in the next cycle when CMTOUT is inverted from 0 to 1. A clock gating cell 402 includes a latch 403 and an AND gate 404.

In order to generate the channel-local transmission/reception switching signal TRL from the transmission/reception switching signal TR common to all channels by the register (REG) 400 and the compare match timer (CMT) 401, TR is delayed by a delay cycle stored in the register (REG) 400.

As such, the register (REG) 400 and the compare match timer (CMT) 401 constitute a transmission/reception switching timing setting circuit setting transmission/reception switching timings at which the ultrasonic waves are switched from the transmission to the reception independently for each of the plurality of transducers (TD) 109. The compare match timer (CMT) 401 performs a transition from the transmission to the reception by performing a delay by a time corresponding to the value stored in the register (REG) 400 using a switching trigger from the transmission to the reception common to all transducers (TD) 109 as a starting point.

The register (REG) 400 is configured by, for example, a non-volatile memory (read only memory (ROM)), and stores a value corresponding to the transmission/reception switching timing when power is supplied to the transmission/reception switching timing setting circuit including the register (REG) 400 and the compare match timer (CMT) 401 or prior to the transmission/reception of the ultrasonic waves.

Next, an operation of the circuit configuration of FIG. 4 will be described with reference to a timing chart of FIG. 5.

Figure 5:
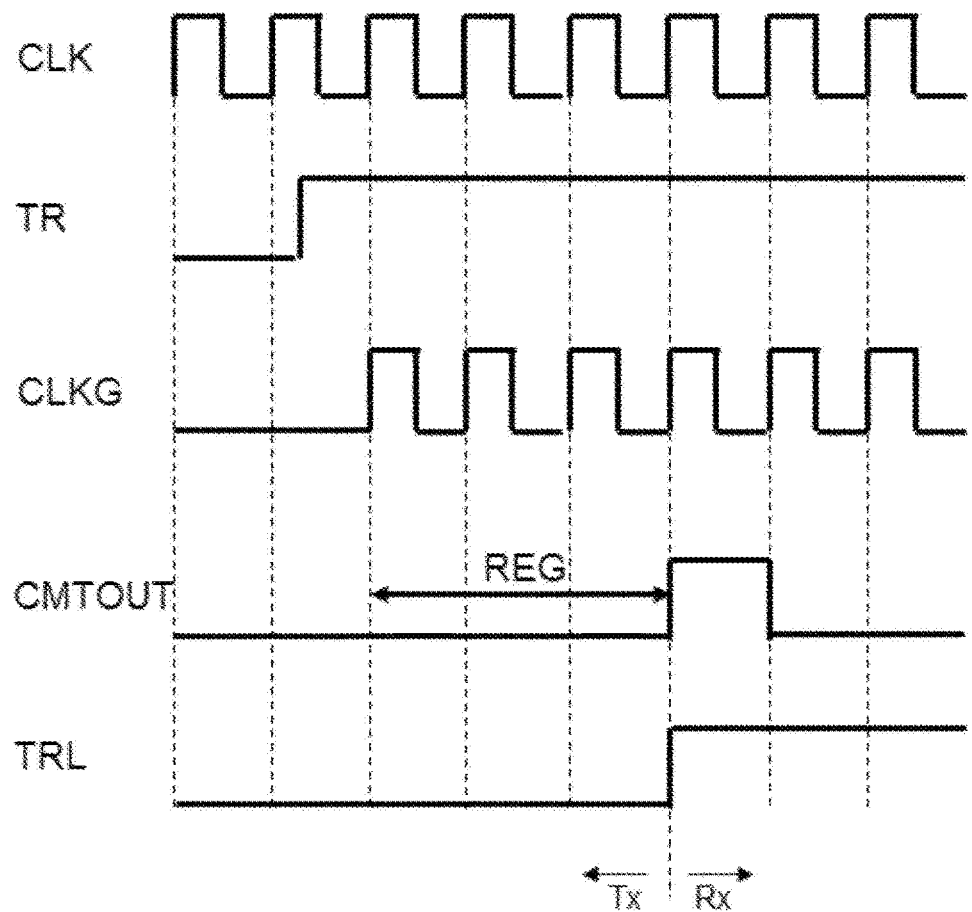
FIG. 5 is a timing chart for describing an operation of the timing circuit including the register and timer circuit of FIG. 4.

As illustrated in FIG. 5, when TR rises, TR passes through the clock gating cell 402 including the latch 403 and the AND gate 404 in FIG. 4, and a gated clock CLKG starts toggling from a clock CLK rise after TR rises. The compare match timer (CMT) 401 is counted up with CLKG, and a CMT output CMTOUT becomes a Hi level in a cycle in which the value stored in the register (REG) 400 and a count value of the compare match timer CMT 401 coincide with each other. As such, counting-up is performed from the CLK rise after TR rises, and after a clock cycle of the value of the register (REG) 400, the count value of the compare match timer (CMT) 401 coincides with the value of the register (REG) 400, such that CMTOUT becomes the Hi level.

Even though it also depends on a configuration of the compare match timer (CMT) 401, if CMTOUT becomes Hi only in the cycle in which the count value coincides with the value of the register (REG) 400, CMTOUT falls to Lo at the next CLKG rise, such that it is necessary to hold the Hi level thereafter. By using the flip flop 405 inverting a value at a rise of CMTOUT, the channel-local transmission/reception switching signal TRL can be held at the Hi level.

As described above, by storing different values in the registers (REG) 400 of the respective channels on the basis of the transmission/reception switching signal TR common to all channels, the TRLs of the respective channels rise after delays of predetermined clock cycles, and the respective channel perform transmission/reception switching using the TRLs. Thus, switching timings of the ultrasonic waves from the transmission to the reception can be set independently and arbitrarily (randomly) for each transducer.

Next, a circuit configuration that writes data to a register 607 of each channel (CH) 604 for implementing the first embodiment as a 2D array probe circuit and an operation thereof will be described with reference to FIGS. 6 and 7.

The channel is changed, and data is sequentially written to the register (REG) 400 of FIG. 4 of each channel. The channel is selected by AND of XON and YON and is sequentially changed. It is assumed that the register 607 in each channel is 4 bits, and it is expressed that four flip flops (FF) are stacked to be 4 bits.

It is technically difficult to generate completely random data, but pseudo-random data can be easily generated using a linear feedback shift register (LFSR) 601. In a case where a circuit is configured by an integrated circuit (IC), a port RNDIN may be prepared so that random data can be input from the outside of the IC to allow a multiplexer MUX 602 to select whether to use the pseudo-random data from the LFSR 601 in the IC or to input external random data.

In the first embodiment, the transmission/reception switching is delayed by a random cycle for each channel with respect to the same delay profile 101 as that of the transmission. In order to realize such a delay, as illustrated in FIG. 6, transmission/reception switching timing data DATA may be generated by adding the delay profile 101 to either the pseudo-random data from the LFSR 601 or the random data input from the RNDIN by a digital signal processor (DSP) 603 and be sequentially written to the register 607 in each channel.

A selection signal XON for each row and a control signal YON for each column are wired, a channel CH in which XON is Hi and YON is Hi is selected by an AND gate 605 and data is written to a register 607 through a circuit 606, and a target CH 604 to which data is to be written is switched by XON and YON and data is sequentially written in the register 607 of each channel.

Figure 7:
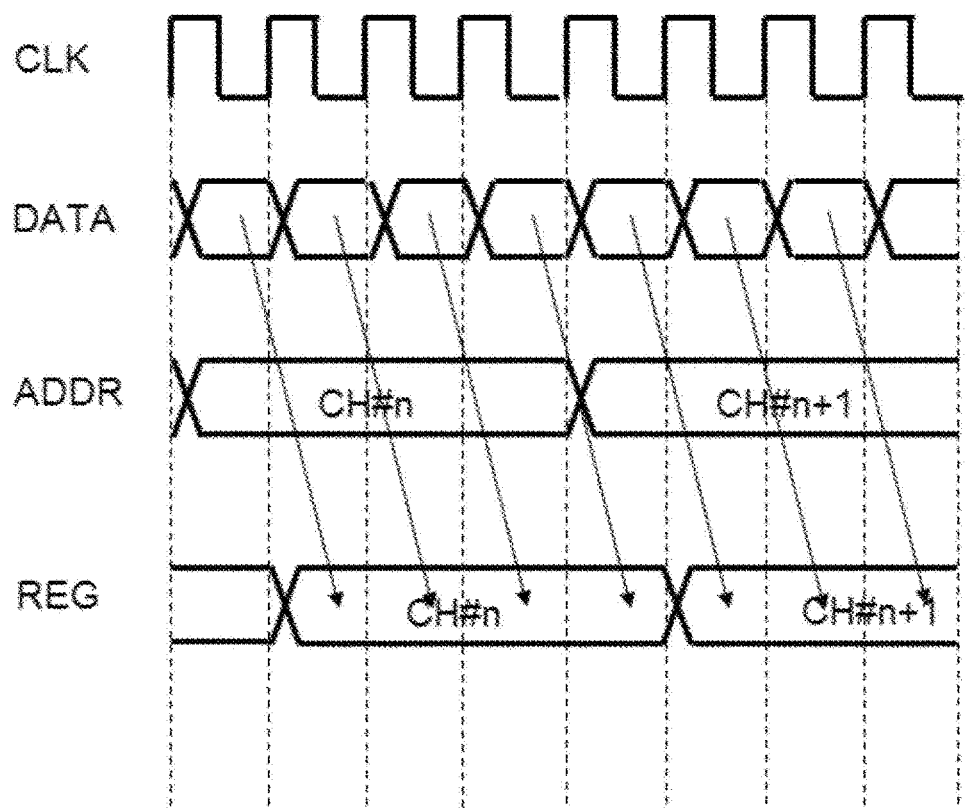
FIG. 7 is a timing chart for describing an operation of the circuit configuration of FIG. 6.

FIG. 7 is a timing chart in which it is assumed that the register 607 in each channel is 4 bits and it is assumed that 4 bits are sequentially written one by one over 4 cycles.

As illustrated in FIG. 7, the register of each channel is 4 bits, but a channel address ADDR is controlled by XON, YON, and data is written to a register of a specified channel CH over 4 cycles. This is sequentially performed by switching channel addresses to write data to registers in all channels.

Figure 6:
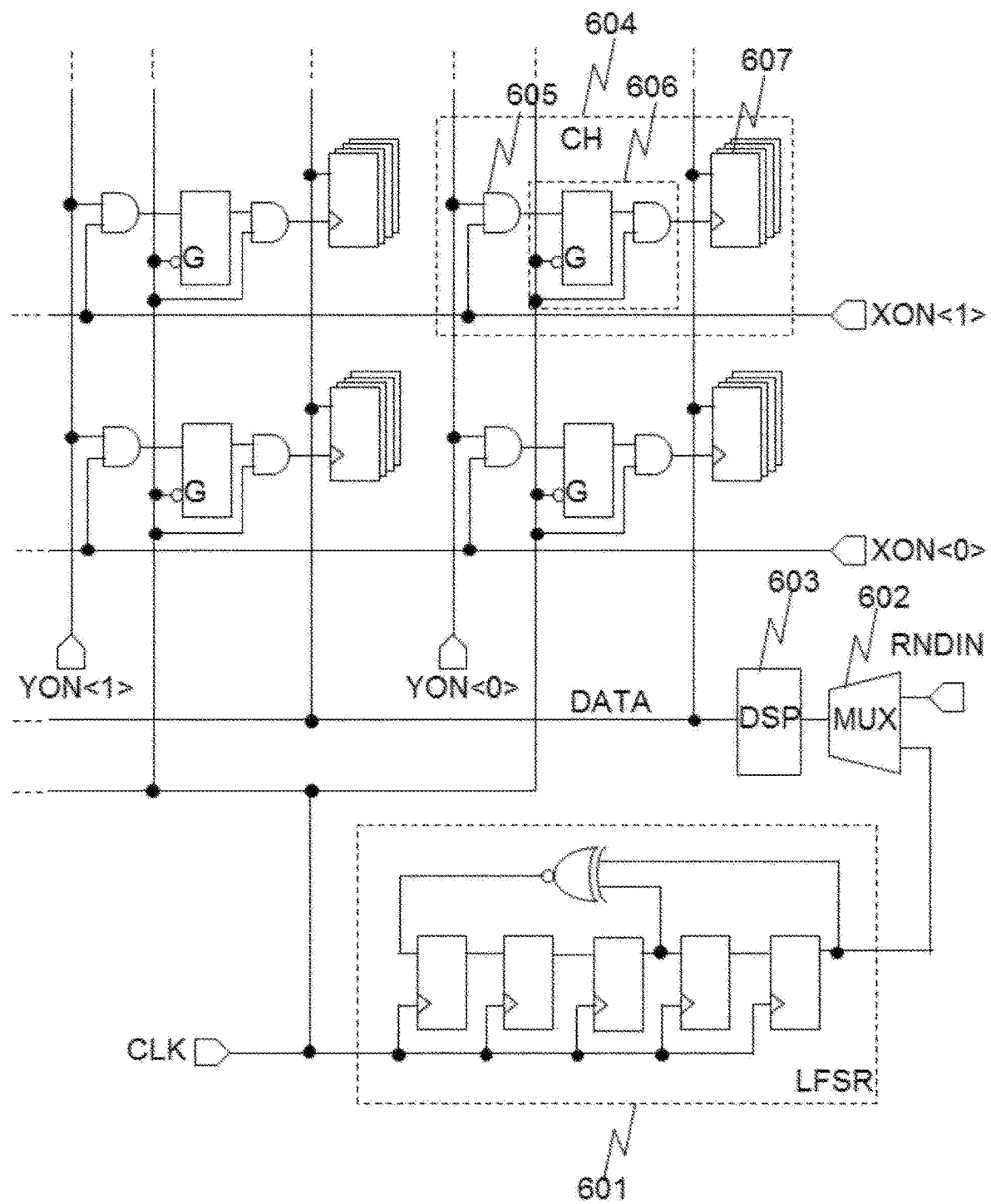
FIG. 6 is a diagram illustrating a circuit configuration writing transmission/reception switching timing data to a register in each channel.

It is assumed in FIGS. 6 and 7 that DATA is a serial data string, but in a case where a restriction of a time for writing the data to all channels cannot be satisfied prior to the transmission, a plurality of LFSRs 601 are prepared. Then, pseudo-random data may be generated as parallel data by changing initial values of flip flops in the LFSRs 601 and be transferred to each channel by buses that are not serial to shorten a writing time.

Second Embodiment

Figure 8A:
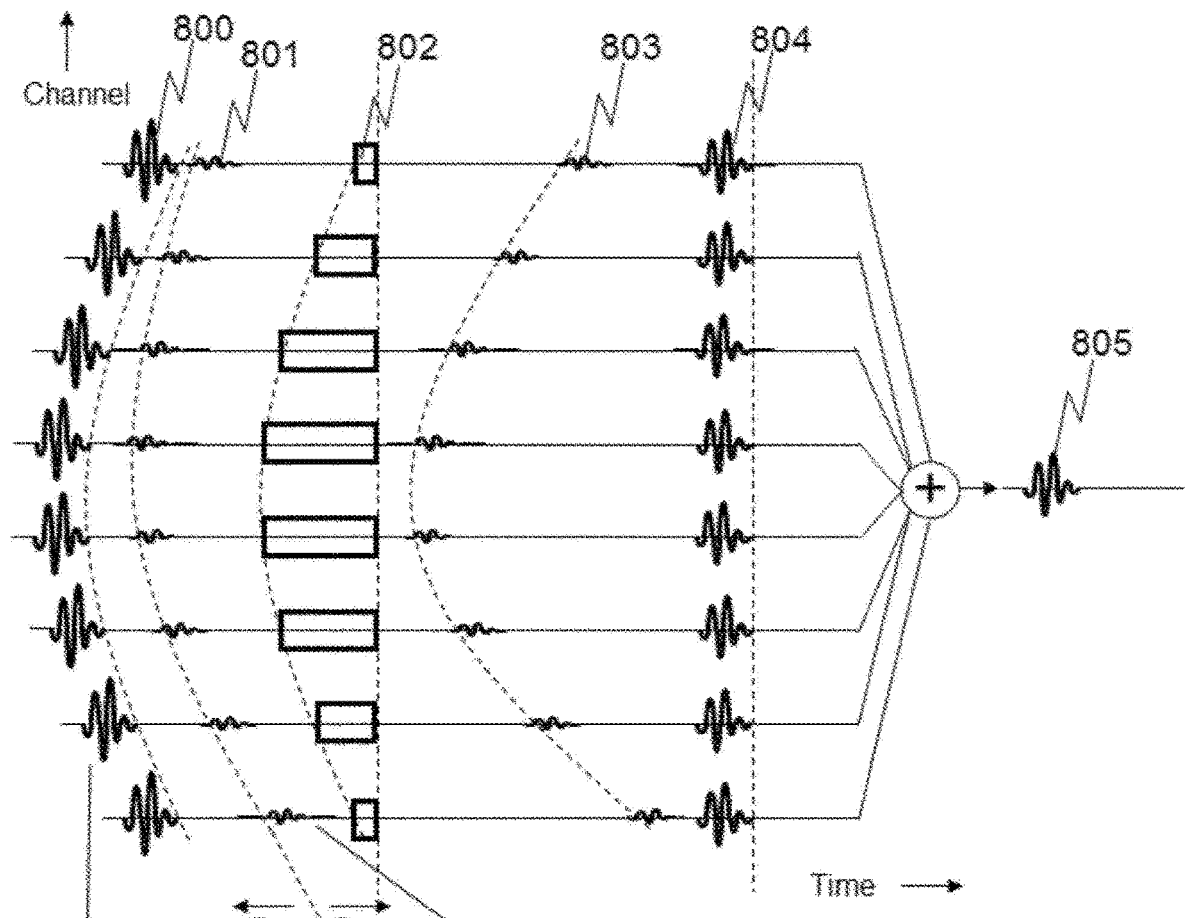
FIG. 8A is a diagram illustrating an operation of an ultrasonic probe according to a second embodiment.
Figure 8B:
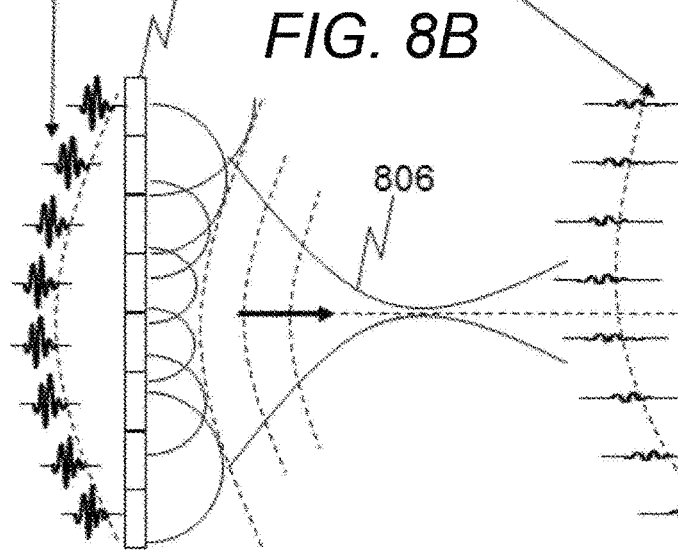
FIG. 8B is a diagram illustrating electro-acoustic conversion of transmission pulses illustrated in FIG. 8A and a spatial behavior of a transmission beam.

An ultrasonic wave transmission/reception switching method in an ultrasonic probe according to a second embodiment will be described with reference to FIGS. 8A to 8C. Here, a horizontal axis of FIG. 8A is time, and a vertical axis of the FIG. 8A corresponds to a spatial arrangement of transducers (TD) 808. The respective waveforms indicate electrical signals of channels of the respective transducers (TD) 808.

In the first embodiment, since the random data is used, an effect depends on a range of the random data and the number of stages of the LFSR 601, and an experimental trial is required because of the randomness. In the second embodiment illustrated in FIG. 8A, it is possible to perform a design in consideration of beam characteristics without using random data.

The second embodiment can be realized by changing data written in the register (REG) 400 without changing a configuration in which the register (REG) 400 and the compare match timer (CMT) 401 of FIG. 4 are included in each channel.

A desired transmission beam 806 (see FIG. 8B) is formed by transmission pulses 800, and a transmission/reception switching timing is set at a timing at which a direction of the transmission beam 806 and a direction of a beam 807 of sounds generated by transmission/reception switching noises 801 (transmission/reception switching at a timing of a delay plane with a focus direction shifted from the transmission pulses 800) deviate from each other by a predetermined angle θ. Here, the transmission pulses 800 and the transmission/reception switching noises 801 have different delay planes in order to shift the focus direction. The lower the position of the channel, the larger the space between the transmission pulse 800 and the transmission/reception switching noise 801.

The electrical transmission/reception switching noises 801 are input to reception circuits at timings of transmission/reception switching electrical noises 803 after reception delays by reception delays 802, such that they are not coherently added. In addition, the reception delays 802 are set so that the direction of the transmission beam 806 and a direction of a reception focus coincide with each other. However, since the beam 807 of the sounds generated by the transmission/reception switching noises 801 deviates from a main lobe direction of the transmission beam 806 by the angle θ, it is not focused by reception, and a virtual image can be reduced by defocusing. Reception signals are focused, and are coherently aligned with one another and phased and added by echo signals 804 after the reception delays to become a reception echo signal 805 after phasing addition.

As such, the beam 807 by the transmission/reception switching noises 801 has a focus direction deviating from that of the transmission beam 806 by the angle θ. As a result, since reception focus is performed toward a transmission direction, the deviating beam 807 is not focused by the reception and is not received as an echo.

As such, in the ultrasonic probe according to the second embodiment, a timing at which a focusing direction of ultrasonic waves by the transmission/reception switching noises generated when switching the ultrasonic waves from transmission to reception deviates from the main lobe direction of the transmission beam of the ultrasonic waves by the predetermined angle is set as the transmission/reception timing.

In the second embodiment, in the transmission/reception switching noises 801, in order to form an angle, the lower the position of the channel, the longer the time from the transmission to the transmission/reception switching, but since the random data is not used, it is possible to deterministically perform a beam design.

Third Embodiment

Figure 9A:
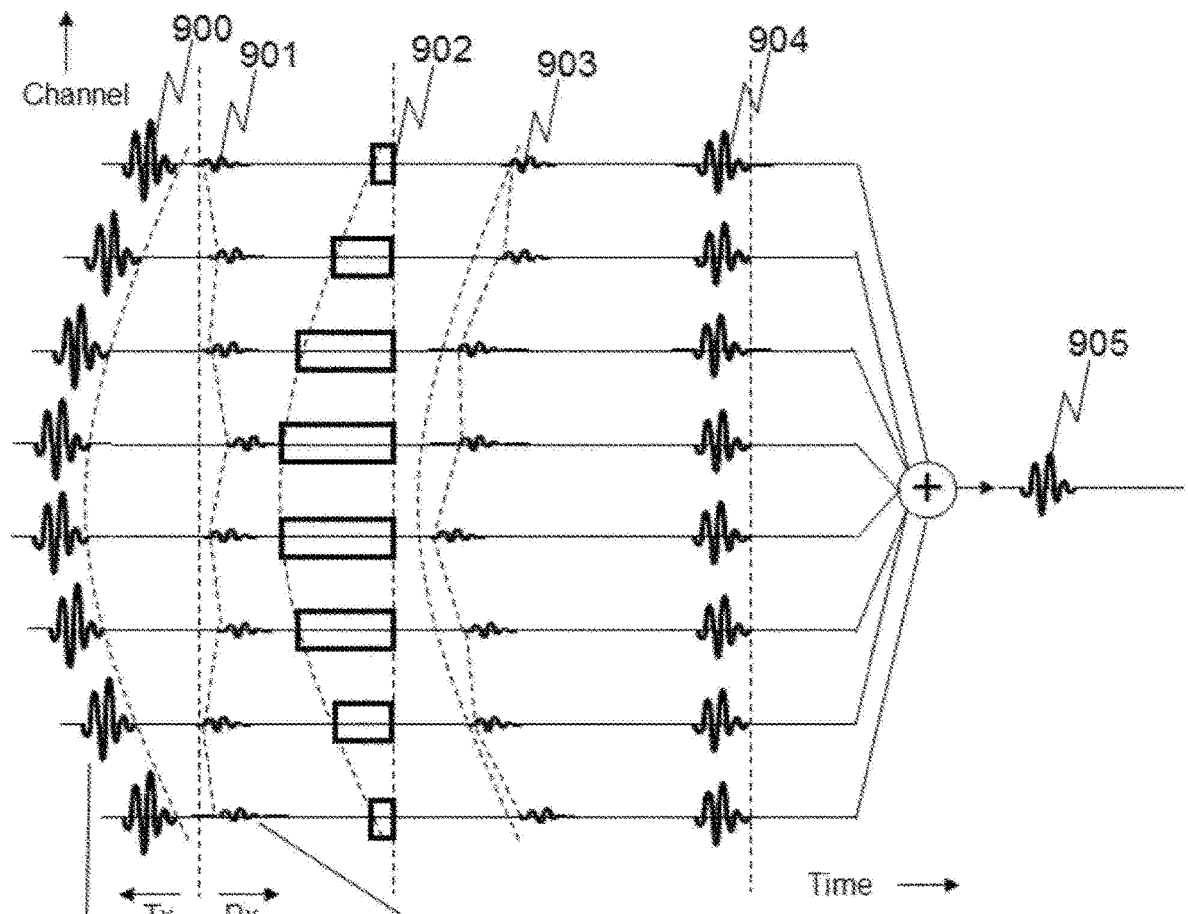
FIGS. 9A to 9C are diagrams illustrating an operation of an ultrasonic probe according to a third embodiment.
Figure 9B:
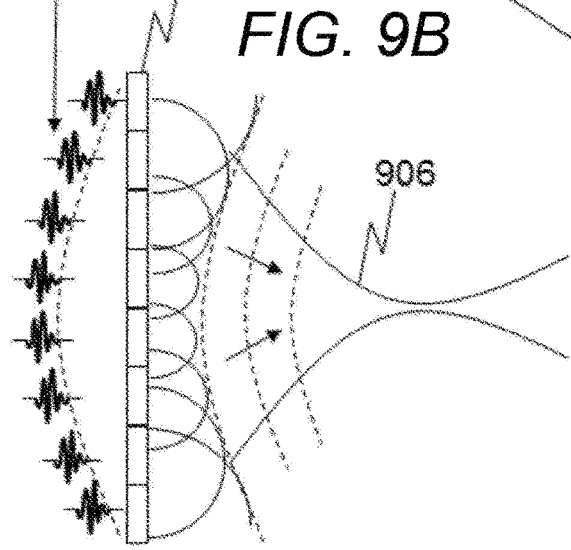

An ultrasonic wave transmission/reception switching method in an ultrasonic probe according to a third embodiment will be described with reference to FIGS. 9A to 9C. Here, a horizontal axis of FIG. 9A is time, and a vertical axis of the FIG. 9A corresponds to a spatial arrangement of transducers (TD) 908. The respective waveforms indicate electrical signals of channels of the respective transducers (TD) 908.

The third embodiment can be realized by changing data written in the register (REG) 400 without changing a configuration in which the register (REG) 400 and the compare match timer (CMT) 401 of FIG. 4 are included in each channel.

In the first embodiment, the DSP 603 of FIG. 6 calculating the same transmission/reception switching timing as the direction of the transmission beam and the random value depending on the transmission beam is required, and it is necessary to write the data to the registers 607 (see FIG. 6) of all channels before each transmission.

In the third embodiment, in order to avoid complexity of hardware and a preparation operation before each transmission, randomization is introduced using a timing of simultaneous transmission/reception switching of all channels as a starting point. In this case, a sound generated by transmission/reception switching noises 901 (addition of random delays to the respective channels based on simultaneous switching of all channels) is randomly disturbed using a plane wave like a random wave front 907 (see FIG. 9C) as a starting point, such that a sound pressure is reduced. Here, reference numeral 902 denotes reception delays, and reference numeral 903 denotes transmission/reception switching electrical noises after the reception delays. In addition, reference numeral 904 denotes echo signals after the reception delays, and reference numeral 905 denotes a reception echo signal after phasing addition. In addition, the wave front illustrated in FIG. 1C is convex to the left, but the wave front illustrated in FIG. 9C is close to a straight line due to delays randomly added based on a straight line.

In addition, in the first embodiment, as illustrated in FIG. 1A, the transmission end channels are switched to the reception, and a delay surface curve is thus the same as the transmission delay. On the other hand, in the third embodiment, as illustrated in FIG. 9A, since the simultaneous transmission/reception switching is performed on all channels, a delay surface is a straight line and the delays are randomly added to the respective channels based on this straight line.

In the third embodiment, a hardware configuration can be simplified, but since the transmission/reception switching is performed simultaneously on all channels, the closer to the center of the position of the channel, the longer the period in which reception is not possible from transmission to transmission/reception switching between transmission pulses 900 and the transmission/reception switching noises 901. However, since random delays are added to the simultaneous transmission/reception switching of all channels, only random data need to be written to the registers (REG) 400 of the respective channels. As a result, a reference delay plane and random calculation (calculation using the DSP 603 of FIG. 6) become unnecessary.

Fourth Embodiment

Figure 10:
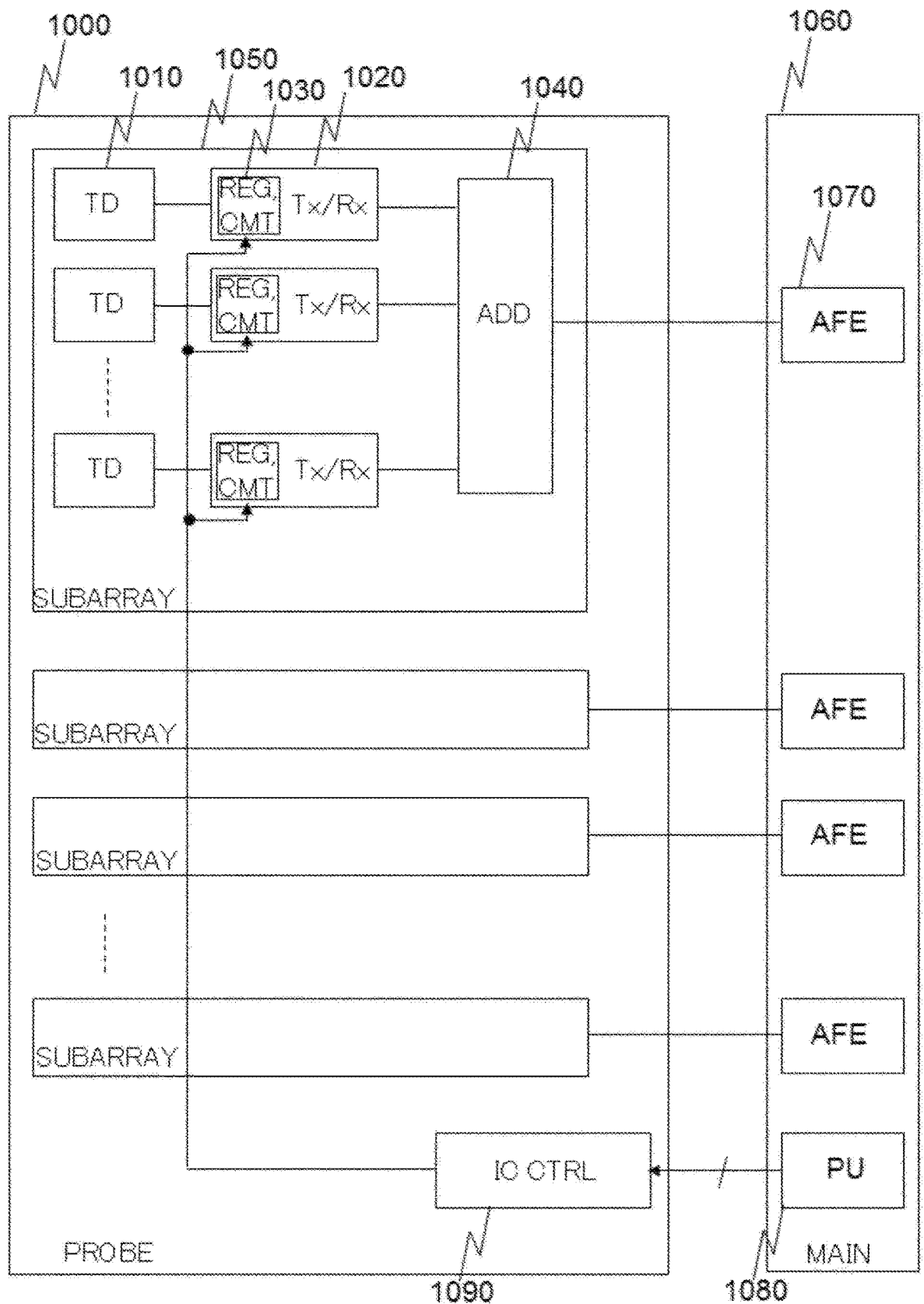
FIG. 10 is a diagram illustrating a configuration of an ultrasonic diagnostic apparatus according to a fourth embodiment.

A configuration of an ultrasonic diagnostic apparatus according to a fourth embodiment will be described with reference to FIG. 10.

The ultrasonic diagnostic apparatus according to the fourth embodiment includes an ultrasonic probe 1000 having transducers arranged in a two-dimensional array for three-dimensional image capturing and a main body device 1060. In the ultrasonic probe 1000, transmission/reception circuits (Tx/Rx) 1020 are arranged for the respective transducers (TD) 1010, and reception signals are added by an addition circuit (ADD) 1040 and are sent to an analog front end (AFE) 1070 in the main body device (MAIN) 1060. Here, a grouping unit of transducer channels to be added is referred to as a subarray (SUBARRAY) 1050. The subarray (SUBARRAY) 1050 is a unit of channel addition in the ultrasonic probe 1000.

A processor (PU) 1080 in the main body device 1060 is a logic circuit that calculates a focus delay. The processor (PU) 1080 sends a control signal to a control logic circuit (IC CTRL) 1090 of an IC in the ultrasonic probe 1000, and the control logic circuit (IC CTRL) 1090 controls a delay for transmission/reception switching or ultrasonic wave focusing according to the control signal. In addition, the control logic circuit (IC CTRL) 1090 also controls a transmission/reception switching timing, and transfers transmission/reception switching timing data to a register (REG) of a register/compare match timer circuit 1030 in each channel. Here, the register/compare match timer circuit 1030 corresponds to the circuit of FIG. 4, and includes the register (REG) 400 and the compare match timer (CMT) 401.

Although not particularly limited, in a case where a transmission circuit is a pulsar type rather than a linear amplifier type, since a waveform is sent to a pulsar as a digital value, the control logic circuit (IC CTRL) 1090 includes a waveform memory that stores waveform data transmitted by the pulsar.

Figure 11:
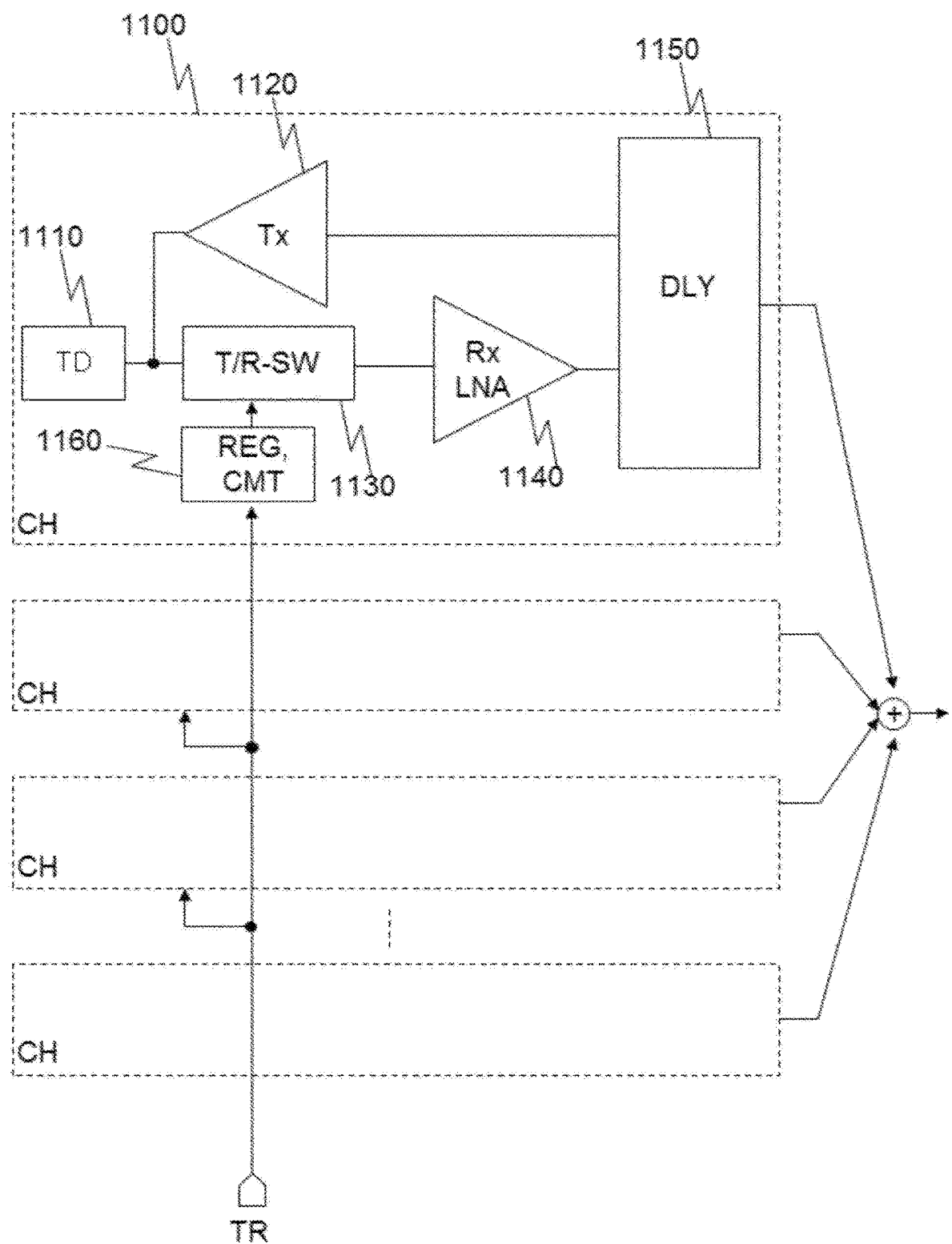
FIG. 11 is a diagram illustrating a configuration of a sub-array in the ultrasonic probe.

Next, a configuration in the subarray 1050 will be described with reference to FIG. 11.

A transmission/reception circuit 1100 per transducer includes a transmission circuit (Tx) 1120 that is configured by a high withstand voltage metal oxide semiconductor (MOS) to generate a high voltage signal and drives the transducer (TD) 1110, a transmission/reception separation switch (T/R-SW) 1130 that becomes a turn-off state at the time of transmission to protect a low voltage reception circuit from the high voltage signal and passes a minute signal therethrough at the time of reception, a low voltage reception low noise amplifier (LNA) 1140, and a minute delay circuit (DLY) 1150 that delays a transmission signal to perform beam forming and delays a reception signal to perform phasing.

The transmission circuit (Tx) 1120 generates a high voltage pulse to drive the transducer (TD) 1110. The transmission/reception separation switch (T/R-SW) 1130 is turned off at the time of the transmission and turned on at the time of reception to protect the reception circuit from a high voltage pulse. The minute delay circuit (DLY) 1150 delays an analog signal.

The reception signal phased by the minute delay circuit (DLY) 1150 are added and transmitted to the main body device 1060. A register and timer (REG/TIMER) 1160 is arranged in each channel corresponding to one transducer, receives a transmission/reception switching signal TR (corresponding to TR of FIG. 4) common to all channels, and delays a transmission/reception switching timing by a value stored in the register (REG) in each channel.

As such, the ultrasonic diagnostic apparatus according to the fourth embodiment includes the ultrasonic probe 1000 that includes a plurality of transducers 1010 that perform electro-acoustic conversion on transmission pulses applied thereto to form a transmission beam, transmission/reception circuits 1020 that are provided so as to correspond to each of the plurality of transducers 1010 and have transmission/reception switching timing setting circuits 1030 (register/compare match timer circuits 1030) setting transmission/reception switching timings at which ultrasonic waves are switched from transmission to reception independently for each of the plurality of transducers 1010, an addition circuit 1040 that adds outputs of a plurality of transmission/reception circuits 1020, and a control circuit (control logic circuit (IC CTRL) 1090) that controls the transmission/reception switching timings; and a main body device 1060 that receives an output of the addition circuit 1040 and transmits a predetermined control signal to the control circuit 1090.

Figure 1C:
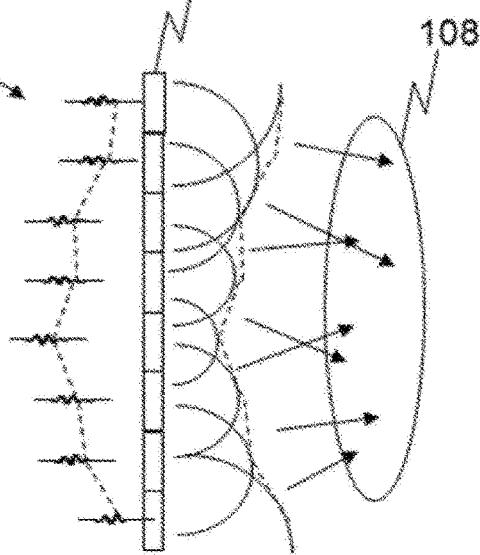
FIG. 1C is a diagram illustrating electro-acoustic conversion of transmission/reception switching noises illustrated in FIG. 1A and a spatial behavior of the transmission/reception switching noises subjected to the acoustic conversion.
Figure 9C:
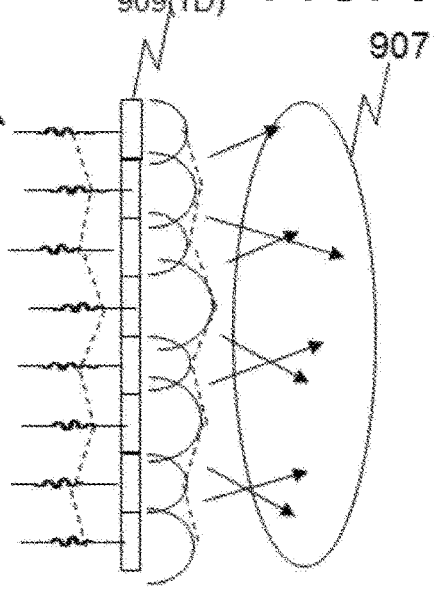

The control circuit 1090 controls the transmission/reception switching timing setting circuits 1030 to set timings at which a focusing direction of the ultrasonic waves by transmission/reception switching noises generated when switching the ultrasonic waves from the transmission to the reception becomes a random direction, as the transmission/reception switching timings (see FIGS. 1C and 9C). In addition, the control circuit 1090 controls the transmission/reception switching timing setting circuits 1030 to set the transmission/reception switching timings so as to be randomly or pseudo-randomly shifted between the transducers 1010.

Figure 8C:
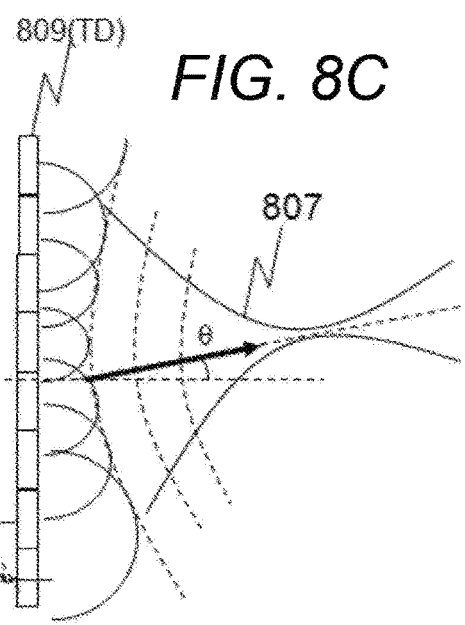
FIG. 8C is a diagram illustrating electro-acoustic conversion of transmission/reception switching noises illustrated in FIG. 8A and a beam as a spatial behavior of the transmission/reception switching noise subjected to the acoustic conversion.

In addition, the control circuit 1090 controls the transmission/reception switching timing setting circuits 1030 to set timings at which a focusing direction of the ultrasonic waves by the transmission/reception switching noises generated when switching the ultrasonic waves from the transmission to the reception deviates from a main lobe direction of the transmission beam of the ultrasonic waves by a predetermined angle, as the transmission/reception switching timings (see FIG. 8C).

In addition, the control circuit 1090 controls the transmission/reception switching timing setting circuits 1030 to set timings at which sounds generated by the transmission/reception switching noises generated when switching the ultrasonic waves from the transmission to the reception are not focused on one point, as the transmission/reception switching timings. In addition, the control circuit 1090 controls the transmission/reception switching timing setting circuits 1030 to perform a transition from the transmission to the reception by performing delays by a time corresponding to values stored in registers using a switching trigger from the transmission to the reception common to all transducers 1010 as a starting point. Note that the control circuit 1090 writes values corresponding to the transmission/reception switching timings to the registers (REG) when power is supplied to the transmission/reception switching timing setting circuits 1030 or prior to the transmission/reception of the ultrasonic waves.

According to the fourth embodiment, it is possible to reduce a virtual image generated because the transmission/reception switching noises generated according to the switching of the ultrasonic waves from the transmission to the reception are electro-acoustically converted by the transducers and are transmitted as unnecessary sounds to the living body and the echoes reflected in the living body are received. That is, it is possible to realize an ultrasonic diagnostic apparatus that can perform ultrasonic image capturing with a little virtual image and a high reliability.

Furthermore, according to the fourth embodiment, in the ultrasonic probe that is a component of the ultrasonic diagnostic apparatus, it is possible to reduce an influence of the virtual image generated because the electrical noises generated in a case of performing the switching of the ultrasonic waves from the transmission to the reception are converted into the sounds by the transducers and are propagated and reflected in the living body, using the respective transducers repeatedly arranged in an array type in one or two dimensions.

In the above embodiment, the virtual image generated because the transmission/reception switching noises generated according to the transmission/reception switching of the ultrasonic waves are converted into the sounds and transmitted to the living body and are reflected from a tissue interface in the living body is reduced. For this reason, it is possible to control the transmission/reception switching timings so that the sounds generated by the transmission/reception switching noises are not strongly focused on one point. In addition, even in a case where the sounds generated by the transmission/reception switching noises are strong and are transmission-focused on one point, it is possible to focus (defocus) the sounds in a scanning angle direction different from that of a reception focus. In addition, the transmission/reception switching timings are controlled for each transducer so that the sounds generated by the switching noises from the transmission to the reception are not strongly focused on one point to randomly propagate a wave front, such that a sound pressure can be weakened.

As such, according to the above embodiment, by setting the timings at which the ultrasonic wave are switched from the transmission to the reception independently for each of the plurality of transducers to randomly shift the transmission/reception switching timings between the transducers, it is possible to prevent the sounds generated by the transmission/reception switching noises from being strongly focused on one point to weaken the sound pressure. As a result, it is possible to reduce the virtual image due to the sound echoes generated when performing the transmission/reception switching.

What is claimed is:

1. An ultrasonic probe comprising:
a plurality of transducer channels that perform electro-acoustic conversion of transmission pulses applied thereto to generate a transmission beam of transmission beam ultrasonic waves;
a plurality of transmission/reception circuits respectively corresponding to each of the plurality of transducer channels, each transmission/reception circuit including a compare match timer (CMT) and a register coupled to the CMT as a transmission/reception switching timing setting circuit; and
a clock gating cell providing gated clock to the CMT; and
a port that sets the output high when the CMT matches with a value on the register,
wherein the transmission/reception switching timing setting circuits set transmission/reception switching timings at which the plurality of transducer channels are switched from transmission to reception independently,
wherein upon switching the transducer channels from transmission to reception, transmission/reception switching noises having ultrasonic waves are generated from the plurality of transducer channels,
wherein the transmission/reception switching timing setting circuits set the transmission/reception switching timings at which the plurality of transducer channels are switched such that respective focusing directions of the ultrasonic waves of the transmission/reception switching noises generated when switching the plurality of transducer channels from transmission to reception are random directions instead of focusing on a point, and
wherein the switching is delayed by a random cycle for each transducer channel by transmission/reception switching timing data written to each register of each channel.

2. The ultrasonic probe according to claim 1,
wherein the transmission/reception switching timing setting circuits set the transmission/reception switching timings at which the transducer channels are switched such that respective focusing directions of the ultrasonic waves of the transmission/reception switching noises generated when switching the transducer channels from transmission to reception deviate from a main lobe direction of the transmission beam of the ultrasonic waves by a predetermined angle.

3. The ultrasonic probe according to claim 1, wherein each transmission/reception switching timing setting circuit includes:
a timer circuit that is connected to the register,
the timer circuit performing a transition from the transmission to the reception by performing a delay by a time corresponding to the transmission/reception switching timing data written to the respective register using a switching trigger from the transmission to the reception common to all the transducer channels as a starting point.

4. The ultrasonic probe according to claim 3,
wherein the register is a non-volatile memory.

5. An ultrasonic diagnostic apparatus comprising:
an ultrasonic probe that includes:
a plurality of transducer channels that perform electro-acoustic conversion of transmission pulses applied thereto to form a transmission beam,
a plurality of transmission/reception circuits respectively corresponding to each of the plurality of transducer channels, each transmission/reception circuit including a compare match timer (CMT) and a register coupled to the CMT as a transmission/reception switching timing setting circuit; and
a clock gating cell providing gated clock to the CMT; and
a port that sets the output high when the CMT matches with a value on the register,
an addition circuit that adds outputs of the plurality of transmission/reception circuits, and
a control circuit that controls the transmission/reception switching timings; and
a main body device that receives an output of the addition circuit and transmits a predetermined control signal to the control circuit,
wherein the transmission/reception switching timing setting circuits set transmission/reception switching timings at which the plurality of transducer channels are switched from transmission to reception independently,
wherein upon switching the transducer channels from transmission to reception, transmission/reception switching noises having ultrasonic waves are generated from the plurality of transducer channels,
wherein the control circuit controls the transmission/reception switching timing setting circuits to set the transmission/reception switching timings at which the plurality of transducer channels are switched such that respective focusing directions of the ultrasonic waves of the transmission/reception switching noises generated when switching the plurality of transducer channels from transmission to reception are random directions instead of focusing on a point, and
wherein the switching is delayed by a random cycle for each transducer channel by transmission/reception switching timing data written to each register of each channel.

6. The ultrasonic diagnostic apparatus according to claim 5,
wherein the control circuit controls the transmission/reception switching timing setting circuits to set the transmission/reception switching timings at which the transducer channels are switched such that respective focusing directions of the ultrasonic waves by transmission/reception switching noises generated when switching the transducer channels from the transmission to the reception deviate from a main lobe direction of the transmission beam of the ultrasonic waves by a predetermined angle.

7. The ultrasonic diagnostic apparatus according to claim 5,
wherein each the transmission/reception switching timing setting circuit includes:
a timer circuit that is connected to the register, and wherein the control circuit controls the transmission/reception switching timing setting circuits to perform a transition from the transmission to the reception by performing a delay by a time corresponding to the transmission/reception switching timing data written to the respective register using a switching trigger from the transmission to the reception common to all the transducer channels as a starting point.

8. The ultrasonic diagnostic apparatus according to claim 7, wherein the register is a non-volatile memory.

9. The ultrasonic probe according to claim 1, further comprising:
a linear feedback shift register (LFSR);
a multiplexer coupled to the LFSR;
a port coupled to the multiplexer; and
a digital signal processor coupled to the LFSR,
wherein the transmission/reception switching timing data is generated by adding a delay profile to one of pseudo-random data from the LFSR and random data input via the port by the digital signal processor, the transmission/reception switching timing data being sequentially written to each register of each channel.

10. The ultrasonic diagnostic apparatus according to claim 5, further comprising:
a linear feedback shift register (LFSR);
a multiplexer coupled to the LFSR;
a port coupled to the multiplexer; and
a digital signal processor coupled to the LFSR,
wherein the transmission/reception switching timing data is generated by adding a delay profile to one of pseudo-random data from the LFSR and random data input via the port by the digital signal processor, the transmission/reception switching timing data being sequentially written to each register of each channel.

* * * * *